US010542938B2

(12) United States Patent
Heismann et al.

(10) Patent No.: US 10,542,938 B2
(45) Date of Patent: Jan. 28, 2020

(54) MEDICAL IMAGING UNIT, MEDICAL IMAGING DEVICE WITH A MEDICAL IMAGING UNIT, AND METHOD FOR DETECTING A PATIENT MOVEMENT

(71) Applicants: Björn Heismann, Erlangen (DE); Martin Nisznansky, Möhrendorf (DE); Steffen Schröter, Fürth (DE); Johann Sukkau, Herzogenaurach (DE)

(72) Inventors: Björn Heismann, Erlangen (DE); Martin Nisznansky, Möhrendorf (DE); Steffen Schröter, Fürth (DE); Johann Sukkau, Herzogenaurach (DE)

(73) Assignee: Siemens Aktiengesellschaft, München (DE)

( * ) Notice: Subject to any disclaimer, the term of this patent is extended or adjusted under 35 U.S.C. 154(b) by 72 days.

(21) Appl. No.: 14/821,423

(22) Filed: Aug. 7, 2015

(65) Prior Publication Data
US 2016/0038090 A1 Feb. 11, 2016

(30) Foreign Application Priority Data

Aug. 7, 2014 (DE) .................... 10 2014 215 651

(51) Int. Cl.
*A61B 5/055* (2006.01)
*A61B 5/11* (2006.01)
(Continued)

(52) U.S. Cl.
CPC ............ *A61B 5/721* (2013.01); *A61B 5/0059* (2013.01); *A61B 5/055* (2013.01); *A61B 5/1113* (2013.01);
(Continued)

(58) Field of Classification Search
None
See application file for complete search history.

(56) References Cited

U.S. PATENT DOCUMENTS 5,376,796 A * 12/1994 Chan .................. G01B 11/2433
250/363.02
2005/0113673 A1 5/2005 Avinash et al.
(Continued)

FOREIGN PATENT DOCUMENTS

CN 102038514 A 5/2011
CN 103654784 A 3/2014
(Continued)

OTHER PUBLICATIONS

German Office Action for related German Application No. 10 2014 215 651.3, dated May 6, 2015, with English Translation.
(Continued)

*Primary Examiner* — Patricia J Park
(74) *Attorney, Agent, or Firm* — Lempia Summerfield Katz LLC

(57) ABSTRACT

A medical imaging unit includes a patient receiving area, a housing unit at least partly surrounding the patient receiving area, a detector unit, and a movement detection unit. The movement detection unit includes two or more detection elements configured for detecting a distance from the detection elements to the patient, and including an evaluation unit. The evaluation unit is configured to establish from detected movement of the individual detection elements a three-dimensional movement of the patient within the patient receiving area.

10 Claims, 2 Drawing Sheets

(51) Int. Cl.
*A61B 5/00* (2006.01)
*G16H 40/63* (2018.01)
*A61B 6/03* (2006.01)
*A61B 6/00* (2006.01)

(52) U.S. Cl.
CPC .......... *A61B 5/1126* (2013.01); *A61B 5/6886* (2013.01); *A61B 5/6891* (2013.01); *G16H 40/63* (2018.01); *A61B 5/1114* (2013.01); *A61B 5/1128* (2013.01); *A61B 5/7271* (2013.01); *A61B 6/037* (2013.01); *A61B 6/527* (2013.01); *A61B 2562/04* (2013.01)

(56) References Cited

U.S. PATENT DOCUMENTS

| | | | |
|---|---|---|---|
| 2006/0170421 A1* | 8/2006 | Benz | G01R 33/563 324/309 |
| 2009/0037130 A1 | 2/2009 | Feiweier et al. | |
| 2010/0191100 A1* | 7/2010 | Anderson | A61B 5/055 600/424 |
| 2011/0105883 A1* | 5/2011 | Lake | A61B 5/0059 600/410 |
| 2012/0320178 A1* | 12/2012 | Siegert | G01R 33/56509 348/77 |
| 2013/0320234 A1* | 12/2013 | Volokh | A61B 6/037 250/453.11 |
| 2014/0016750 A1 | 1/2014 | Kang et al. | |
| 2014/0073904 A1 | 3/2014 | Biber | |
| 2015/0036150 A1* | 2/2015 | Kobayashi | A61B 1/0005 356/614 |
| 2016/0073962 A1* | 3/2016 | Yu | A61B 5/721 600/407 |

FOREIGN PATENT DOCUMENTS

| | | | | |
|---|---|---|---|---|
| DE | 102007034955 A1 | 2/2009 | | |
| GB | 2452065 A | * | 2/2009 | .......... A61B 5/1126 |
| WO | WO2007136745 A2 | 11/2007 | | |

OTHER PUBLICATIONS

PMD-sensor, photonic mixer device; From Wikipedia, the free encyclopedia, Jul. 11, 2011.
Chinese Office Action for Chinese Patent Application No. 201510463220.2 dated May 3, 2017, with English Translation.
Chinese Office Action for Chinese Application No. 201510463220.2, dated Jan. 3, 2018, with English Translation.

* cited by examiner

MEDICAL IMAGING UNIT, MEDICAL IMAGING DEVICE WITH A MEDICAL IMAGING UNIT, AND METHOD FOR DETECTING A PATIENT MOVEMENT

This application claims the benefit of DE 10 2014 215 651.3, filed on Aug. 7, 2015, which is hereby incorporated by reference in its entirety.

BACKGROUND

The present embodiments relate to a medical imaging device.

In medical imaging examinations that use a long scanning time, such as, for example, magnetic resonance examinations, SPECT examinations, PET examinations, etc., a patient movement may lead to artifacts in the medical slice images. A correction of this patient movement in the detected medical data may at least reduce these artifacts.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a patient movement is accurately detected during a medical imaging.

One or more of the present embodiments are based on a medical imaging unit including a patient receiving area, a housing unit at least partly surrounding the patient receiving unit, a detector unit, and a movement detection unit. The movement detection unit includes at least two or more detection elements configured to detect a distance between the detection elements and the patient, and including an evaluation unit. The evaluation unit is configured to establish a three-dimensional movement of the patient within the patient receiving area from the detected distance data.

This enables a cost-effective movement detection that makes a reliable and rapid detection of a movement of the patient within the patient receiving area possible to be provided. In one embodiment, the two or more detection elements are read out with a high temporal resolution, so that an especially exact and always current position change and/or movement (e.g., a three-dimensional movement) of the patient may be detected for a medical imaging examination. The established patient movement enables the movement of the patient to be taken into account during an evaluation of medical image data of the medical imaging examination, and in this way, artifacts in medical slice images may be at least reduced and/or suppressed.

In this context, a medical imaging unit may, for example, be a patient tunnel with a housing unit and/or detector unit of a medical imaging device and/or a magnetic resonance coil, etc. surrounding the patient tunnel. Establishing a three-dimensional movement may be the movement and/or the movement data being detected along three different dimensions and/or spatial directions.

In one embodiment, the two or more detection elements are disposed at different positions on the housing unit. In this way, the change in position and/or the movement of the patient may advantageously be detected from different perspectives. For example, the movement along three different dimensions and/or spatial directions may be detected especially easily in this way.

In one embodiment, the movement detection unit includes a detection array including the two or more detection elements. The two or more detection elements, because of an array arrangement (e.g., a matrix arrangement) of the individual detection elements within the detection array, for example, enable an outage of individual detection elements to be easily compensated for. In one embodiment, a distance between two neighboring detection elements (e.g., directly neighboring elements) amounts to a maximum of 20 cm or a maximum of 10 cm.

In one embodiment, the two or more detection elements are disposed at least partly within the housing unit. In this way, a compact and space-saving arrangement of the two or more detection elements within the medical imaging unit may be provided, as may be provided in an embodiment of the detection elements as distance sensors.

For example, the two or more detection elements may be disposed at least partly on a side of the housing unit facing away from the patient receiving area, which enables a space-saving and compact medical imaging unit to be provided. In one embodiment, the housing unit includes transparent part areas for this purpose, which are embodied transparent or permeable for the movement detection signals of the two or more detection elements.

In a further embodiment, the two or more detection elements each have a detection direction, and these detection directions may be aligned on a central axis and/or a center of the patient receiving area. In this way, the individual detection elements may be focused on the patient, and thus, the patient and thereby also a change in position or a movement of the patient may be detected. In this context, a detection direction may be a direction in which a distance is measured by a detection element.

In one embodiment, the two or more detection elements each include a distance sensor, through which the detection elements may be disposed directly on a surface of the housing unit surrounding the patient receiving area. In addition, because of the use of distance sensors as detection elements, for example, problems in connection with a focal length, as occur, for example, with optical cameras, may be prevented.

A cost-effective movement detection unit may be provided if the two or more detection elements each include a position sensitive device (PSD) sensor. In addition, a space-saving arrangement of the movement detection unit may be achieved as a result of the compact design of the PSD sensors. Using the PSD sensors, the position of a light point and/or distances to light points may be detected in one or in two dimensions.

As an alternative to this, one of the at least two detection elements may also include a time-of-flight sensor.

One or more of the present embodiments are based on a medical imaging device with a medical imaging unit. The medical imaging unit includes a patient receiving area, a housing unit at least partly surrounding a patient receiving area, a detector unit, and a movement detection unit. The movement detection unit includes two or more detection elements configured for detecting a distance between the detection elements and the patient, and including an evaluation unit. The evaluation unit is configured to establish a three-dimensional movement of the patient within the patient receiving area from the detected distance data of the individual detection elements. This configuration enables a cost-effective movement detection unit to be provided, which makes possible a reliable and rapid detection of a movement of the patient within the patient receiving area. Using the established patient movement, the movement of the patient may be taken into account in the evaluation of medical image data of the medical imaging examination. In this way, artifacts in medical slice images may be at least reduced and/or suppressed.

The medical imaging device may be formed by all medical imaging devices appearing sensible to the person skilled in the art, in which a medical imaging examination lasts for a longer examination time. In one embodiment, the medical imaging device is formed by a magnetic resonance device, a PET device and/or an SPECT device.

The advantages of the medical imaging device correspond to the advantages of the medical imaging unit that have been explained in detail above. Features, advantages, or alternate forms of embodiments mentioned may likewise be transferred to the other subject matter and vice versa.

In a further embodiment, the medical imaging unit includes a magnetic resonance coil device, through which (e.g., for magnetic resonance examinations) an arrangement (e.g., close to the patient) of the movement detection unit may be achieved. The magnetic resonance coil device may, for example, be formed by a local magnetic resonance coil device (e.g., a head coil device and/or a magnetic resonance coil device installed permanently within the magnetic resonance device), such as a radio-frequency coil unit integrated within a magnet unit.

As an alternative or in addition, the medical imaging unit may also include a patient tunnel of the medical imaging device, so that an advantageous arrangement (e.g., close to the patient) of the movement detection unit within the medical imaging device may be achieved. The patient tunnel may include a housing unit and the patient receiving area, which is surrounded by the housing unit. The patient is disposed in the patient receiving area for a medical imaging examination using a movably supported patient table.

One or more of the present embodiments are further based on a method for detecting a patient movement of a patient able to be disposed within a patient receiving area of a medical imaging unit. The medical imaging unit includes a movement detection unit including two or more detection elements configured to detect a distance between the detection elements and the patient. The method includes using the standard model for a body shape of at least one part area of the patient. The method also includes detecting first distance data using the two or more detection elements for determining a patient model that may deviate from the standard model for the at least one part area of the body shape of the patient. The method includes detecting further distance data using the two or more detection elements. A movement is determined based on the distance data for the patient model.

Through this embodiment, a movement of the patient may be detected especially exactly and may be provided for a correction of medical image data. For example, an extremely reliable determination of the movement of the patient may be provided, since as a result of the body model, even in the event of an outage of one or a number of detection elements, a patient movement may still be reliably determined.

The advantages of the method of the present embodiments essentially correspond to the advantages of the medical imaging unit of the present embodiments, which have been explained in detail above. Features and advantages or alternate forms of embodiments mentioned may likewise be transferred to the other subject matter and vice versa.

DETAILED DESCRIPTION

Figure 1:
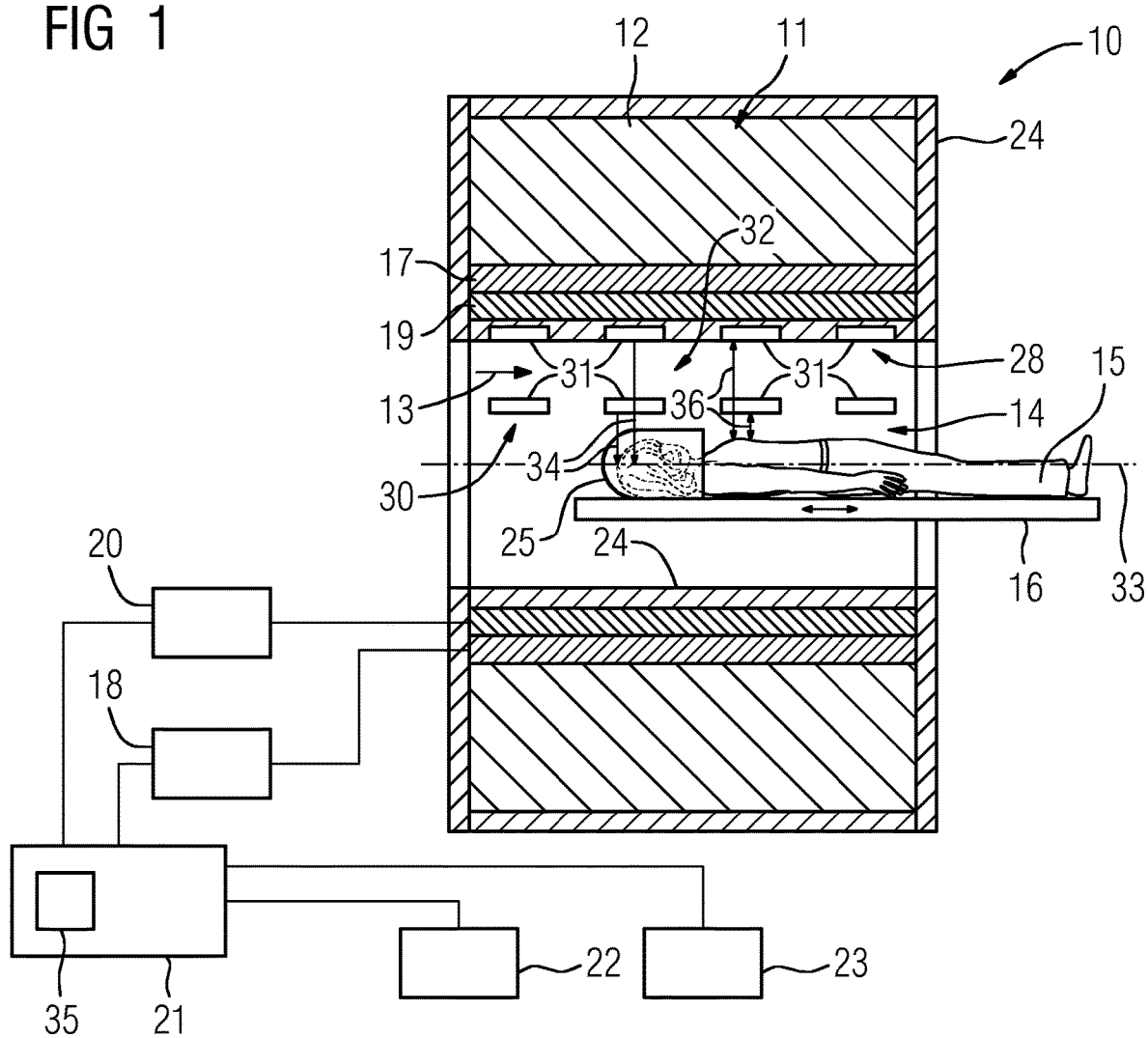
FIG. 1 shows one embodiment of a medical imaging device with a medical imaging unit in a schematic diagram.

FIG. 1 shows a schematic of one embodiment of a medical imaging device 10. In the present exemplary embodiment, the medical imaging device 10 is formed by a magnetic resonance device. The embodiment of the imaging device 10 is not restricted to a magnetic resonance device, however. Instead, the medical imaging device 10 may be formed by all medical imaging devices appearing sensible to the person skilled in the art, such as by a computed tomography device, a Positron Emission Tomography device, a SPECT device, etc., for example.

The magnetic resonance device includes a detector unit formed by a magnet unit 11 with a superconducting main magnet 12 for creating a strong and, for example, constant main magnetic field 13. In addition, the magnetic resonance device includes a patient receiving area 14 for receiving a patient 15. The patient receiving area 14 in the present exemplary embodiment is configured in a cylindrical shape and is surrounded in a circumferential direction by the magnet unit 11 in a cylindrical shape. However, an embodiment of the patient receiving area 14 deviating from this may be provided. The patient 15 may be pushed by the patient support device 16 of the magnetic resonance device into the patient receiving area 14. The magnetic resonance device also includes a housing unit 24 that surrounds the magnet unit 11 and the patient receiving area 14.

The magnet unit 11 also includes a gradient coil unit 17 for creating magnetic field gradients. The gradient coil unit 17 is used for local encoding during imaging. The gradient coil unit 17 is controlled by a gradient control unit 18 of the magnetic resonance device. The magnet unit 11 also includes a radio-frequency antenna unit 19 for exciting a polarization that occurs in the main magnetic field 13 created by the main magnet 12. The radio-frequency antenna unit 19 is controlled by a radio-frequency antenna control unit 20 of the magnetic resonance device and radiates radio-frequency magnetic resonance sequences into an examination area, which is essentially formed by the patient receiving area 14 of the magnetic resonance device.

To control the main magnet 12, the gradient control unit 18 and to control the radio-frequency antenna control unit 20, the magnetic resonance device includes a control unit 21. The control unit 21 centrally controls the magnetic resonance device, such as, for example, carrying out a predetermined imaging gradient echo sequence. In addition, the control unit 21 includes an evaluation unit not shown in any greater detail for an evaluation of image data. Control information, such as imaging parameters, for example, as well as reconstructed magnetic resonance images, may be displayed on a display unit 22, for example, on at least one monitor of the magnetic resonance device for an operator. In addition, the magnetic resonance device includes an input unit 23, by which the information and/or parameters may be entered during a measuring process by an operator.

The magnetic resonance device also includes a local magnetic resonance coil device 25 that, in the present exemplary embodiment, is formed by a head coil device. As an alternative to this, the local magnetic resonance coil device 25 may also be formed by a knee coil device, an arm coil device, a chest coil device, etc.

To detect a movement of the patient 15 during a magnetic resonance examination, the magnetic resonance device includes a medical imaging unit 28. The medical imaging unit 28 includes the radio-frequency antenna unit 19 of the magnet unit 11.

The medical imaging unit 28 is shown in FIG. 1 and includes the patient receiving area 14 of the magnetic resonance device. The medical imaging unit 28 also includes the housing unit 24 surrounding the patient receiving area 14. The radio-frequency antenna unit 19 is, for example, included in a detector unit of the medical imaging unit 28. The medical imaging unit 28 also includes a movement detection unit 30 with the plurality of detection elements 31. The individual detection elements 31 are disposed within a detection array 32 (e.g., a two-dimensional detection array 32) of the movement detection unit 30. To this end, the individual detection elements 31 are disposed at different positions on the housing unit 24 of the medical imaging unit 28. The individual detection elements 31 are disposed at the same distance from one another. The individual detection elements 31 may also be disposed on the housing unit 24 with an arrangement deviating from the above arrangement.

The individual detection elements 31 are configured to detect a distance 36 between the patient 15 (e.g., a part area of the patient 15 disposed within the patient receiving area 14) and the individual detection elements 31. The individual detection elements 31 are each formed by distance sensors (e.g., position sensitive device (PSD)) sensors.

The individual detection elements 31 are disposed and/or integrated within the housing unit 24. The housing unit 24 has transparent part areas that are disposed on a side of the housing unit 24 facing towards the patient receiving area 14 and are embodied for a distance measurement signal of the individual detection elements 31. As an alternative or in addition, the individual detection elements 31 may also be disposed on a side of the housing unit 24 facing towards the patient receiving area 14 and/or be disposed on a side of the housing unit 24 facing away from the patient receiving area 14.

The individual detection elements 31 each have a detection device 34. The individual detection devices 34 of the detection elements 31 are aligned on a central axis 33 and/or a center of the patient receiving area 14 for detecting a distance 36 to the patient 15.

The movement detection unit 30 also includes an evaluation unit 35 configured to establish from the distance data detected by the individual detection elements 31 (e.g., the two-dimensional detection array 32) a three-dimensional movement of the patient 15 that the patient has made within the patient receiving area 14. The evaluation unit 35 is disposed in the present exemplary embodiment within the control unit 21. The evaluation unit 35 may also be disposed separately from the control unit 21.

Figure 2:
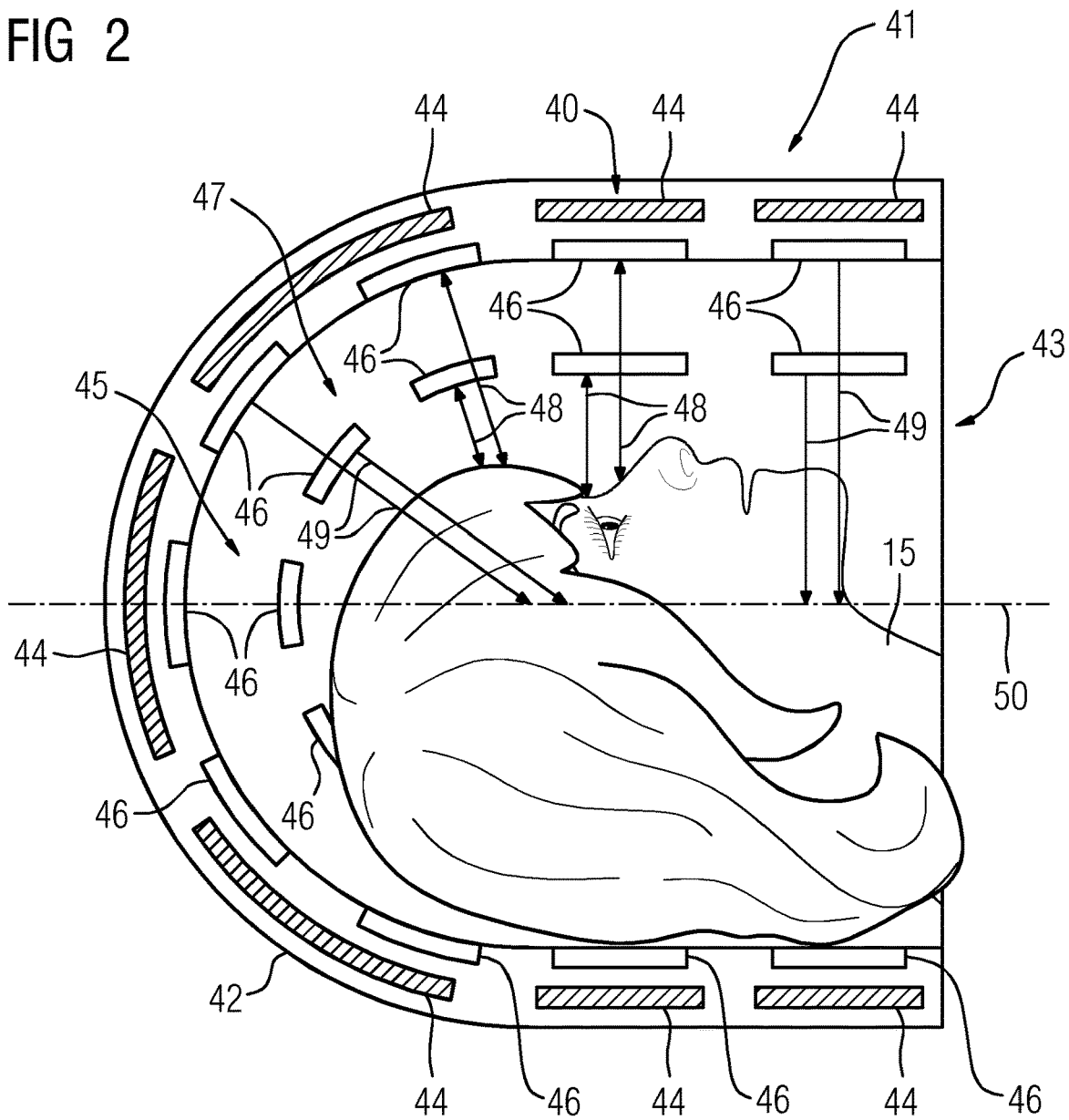
FIG. 2 shows an alternate exemplary embodiment of a medical imaging unit in a schematic diagram.

An alternate exemplary embodiment of the medical imaging unit is shown in FIG. 2. Components, features and functions that essentially remain the same are basically labeled with the same reference characters. The description given below is essentially restricted to the differences from the exemplary embodiment in FIG. 1, where in relation to components, features, and functions that remain the same, see the description of the exemplary embodiment in FIG. 1.

One embodiment of a medical imaging unit 40 is shown in greater detail in FIG. 2. The medical imaging unit 40 includes a local magnetic resonance coil device 41 that, in the present exemplary embodiment, is formed by a head coil unit. As an alternative to this, the local magnetic resonance coil device 41 may also be formed by a knee coil unit, an arm coil unit, a chest coil unit, etc.

The head coil unit includes a housing unit 42 that surrounds a local patient receiving area 43 of the head coil unit in the shape of a skull cap. The head coil unit also includes a detector unit with a number of coil elements 44.

The medical imaging unit 40 (e.g., the head coil device) also includes a movement detection unit 45 with a plurality of detection elements 46. The individual detection elements 46 are disposed within a detection array 47 (e.g., a two-dimensional detection array). The individual detection elements are disposed at different positions on the housing unit 42 of the head coil device. The individual detection elements 46 are disposed with an equal distance between the individual detection elements 46. The individual detection elements 46 may also be disposed on the housing unit 42 in an arrangement deviating from the above arrangement.

The individual detection elements 46 of the head coil device are configured for detecting a distance 48 from the patient 15 (e.g., the part area of the patient 15 disposed within the patient receiving area 43) to the individual detection elements 46. The individual detection elements 46 are each formed by distance sensors (e.g., by PSD sensors).

The individual detection elements 46 are disposed on the housing unit 42. The housing unit 42 includes transparent part areas that are embodied transparent for the distance measurement signal of the individual detection elements 46. The individual detection elements 46 are disposed on a side of the housing unit 42 facing away from the patient receiving area 43 on the transparent part areas of the housing unit 42. As an alternative or in addition, the individual detection elements 46 may also be disposed on a side of the housing unit facing towards the patient receiving area 43 and/or may be integrated within the housing unit 42.

The individual detection elements 46 each have a detection device 49, where the individual detection devices 49 of the detection elements 46 are aligned on a central axis 50 and/or a center of the patient receiving area 43 for detecting the distance 48 to the patient 15.

For an evaluation of the detected distance data of the individual detection elements 46 of the head coil device, the medical imaging unit 40 (e.g., the head coil device) includes an evaluation unit 35. The evaluation unit 35 is disposed within the control units 20 and is shown in greater detail in FIG. 2. In the present exemplary embodiment, the magnetic resonance device includes a single evaluation unit 35 for evaluating the detected distance data of the medical imaging unit 28 having the radio-frequency antenna unit 19 and for evaluating the detected distance data of the medical imaging unit 40 having the head coil device. An embodiment deviating from the above such as, for example, two or more evaluation units may be provided. For evaluating the distance data of the detection elements 46 of the head coil device, the evaluation unit 35 is connected to the individual detection elements 46 for the purposes of exchanging data.

Figure 3:
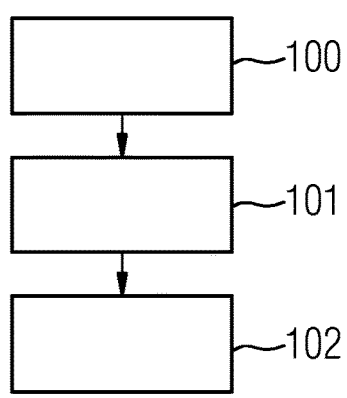
FIG. 3 shows a flowchart of one embodiment of a method for determining a patient movement.

FIG. 3 shows one embodiment of a method for determining a patient movement of the patient 15 at least partly able to be disposed within one of the patient receiving areas 14, 43 of one of the medical imaging units 28, 40 shown in FIG. 1 and/or FIG. 2. The method is controlled autonomously and/or automatically by the evaluation unit 35. The evaluation unit 35 has evaluation software and/or evaluation computer programs provided for this purpose. The evaluation software and/or the evaluation computer programs are stored in a memory unit and are executed for running the method for determining a patient movement by a processor unit of the evaluation unit 35.

In act 100 of the method for determining the patient movement of the patient 15, a standard model for a body shape of at least one part area of the patient 15 who is disposed within one of the patient receiving areas 14, 43 is used. For example, for head examinations on the patient 15, a standard model of the head together with the medical imaging unit 40 described in FIG. 2, which includes the head coil unit, is used. For a torso examination on the patient 15, a standard model of a torso, together with the medical imaging unit 28 described in FIG. 1, may be used. Such standard models may be stored within the memory unit and are autonomously and/or automatically selected by the evaluation unit 35 as soon as the part area of the patient 15 to be examined is defined within the evaluation unit 35 and/all within the control unit 21. In addition, the available standard models include three-dimensional standard models so that with the aid of the three-dimensional standard models, a three-dimensional movement of the patient may be determined and/or detected.

In a further, subsequent method act 101, first distance data is detected by the individual detection elements 31, 46 (e.g., the distance sensors) of the selected and/or used medical imaging unit 28, 40. A patient model for the relevant part area of the patient 15 is then created by the evaluation unit 35 autonomously and/or automatically based on the detected first distance data and the selected standard model. The patient model results from deviations that are produced as a result of the first detected distance data in relation to the standard model. This first distance data is detected once before the magnetic resonance examination. The patient models determined by the evaluation unit 35 may include three-dimensional patient models.

In a further method act 102, further distance data is detected by the respective detection elements 31, 46 (e.g., by the distance sensors). The further distance data is continuously detected during the entire magnetic resonance examination on the patient 15. Movement data of a position change and/or a three-dimensional movement for the patient model (e.g., three-dimensional patient model) is defined and/or established automatically and/or autonomously by the evaluation unit 35 based on the further distance data. The use of the patient model together with the respective detection array 32, 47 of a plurality of detection elements 31, 46 within the respective medical imaging unit 28, 40 makes it possible, even in the event of an outage of individual detection elements 31, 46, to determine a reliable movement of the patient 15.

The determined movement is transmitted from the evaluation unit 35 to the control unit 21 and is taken into account therein in evaluation of the medical image data (e.g., in order to correct the medical image data with respect to an undesired movement of the patient 15 during the imaging examination).

Although the invention has been illustrated and described in greater detail by the exemplary embodiments, the invention is not, however, restricted by the disclosed examples. Other variations may be derived herefrom by the person skilled in the art without departing from the scope of protection of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A medical imaging unit comprising:
   a patient receiving area;
   a head coil comprising a housing having an internal surface with an inner circumference configured to at least partially surround a head of a patient in the patient receiving area; and
   a movement detector system comprising a first plurality of detectors and a second plurality of detectors, wherein the first plurality of detectors is arranged within a two-dimensional detection array disposed on the internal surface of the housing around the inner circumference such that at least one detector of the first plurality of detectors is positioned to face a first surface of the head of the patient and at least one additional detector of the first plurality of detectors is positioned to face a second, opposite surface of the head of the patient, and wherein the second plurality of detectors is arranged within a second, different two-dimensional detection array disposed on the internal surface of the housing,
   wherein each detector of the first plurality of detectors and the second plurality of detectors is configured to detect a distance between the respective detector and the patient,
   wherein the movement detector system is configured to establish, from detected distance data of individual detectors of the first plurality of detectors and the second plurality of detectors, a three-dimensional movement of the patient within the patient receiving area during a medical imaging of the patient, and
   wherein the medical imaging unit is configured to evaluate medical image data using the established three-dimensional movement of the patient, therein reducing artifacts in at least one medical slice image of the medical image data.

2. The medical imaging unit of claim 1, wherein each individual detector of the first plurality of detectors comprises a detection device,
   wherein each detection device is aligned on a central axis, a center of the patient receiving area, or a combination thereof.

3. The medical imaging unit of claim 1, wherein the detectors of the first plurality of detectors are positioned with an equal distance between adjacent detectors.

4. The medical imaging unit of claim 1, wherein each detector of the first plurality of detectors comprises a position sensitive device (PSD) sensor.

5. A medical imaging device comprising:
   a patient receiving area;
   a head coil comprising a housing having an internal surface with an inner circumference configured to at least partially surround a head of a patient in the patient receiving area; and
   a first plurality of detectors arranged within a two-dimensional detection array disposed on the internal surface of the housing around the inner circumference such that at least one detector of the first plurality of detectors is positioned to face a first surface of the head of the patient and at least one additional detector of the first plurality of detectors is positioned to face a second, opposite surface of the head of the patient, and wherein each detector of the first plurality of detectors is configured to detect a distance between the respective detector and the patient;

a second plurality of detectors arranged within a second, different two-dimensional detection array disposed on the internal surface of the housing; and a controller configured to:
    establish, from detected distance data of individual detectors of the first plurality of detectors and the second plurality of detectors, a three-dimensional movement of the patient within the patient receiving area during a medical imaging of the patient; and
    evaluate medical image data using the established three-dimensional movement of the patient, therein reducing artifacts in at least one medical slice image of the medical image data.

6. The medical imaging device of claim 5, further comprising:
    a magnetic resonance coil device.

7. The medical imaging device of claim 5, wherein each individual detector of the first plurality of detectors comprises a detection device, and
    wherein each detection device is aligned on a central axis, a center of the patient receiving area, or a combination thereof.

8. The medical imaging device of claim 5, wherein each detector of the first plurality of detectors comprises a position sensitive device (PSD) sensor.

9. A method for determining a three-dimensional movement of a patient during a magnetic resonance examination of the patient, the patient being disposable within a patient receiving area of a medical imaging unit, wherein the medical imaging unit comprises a movement detection unit having a first plurality of detectors and a second plurality of detectors, wherein the first plurality of detectors is arranged within a two-dimensional detection array disposed on an internal surface of a housing around an inner circumference of the housing such that at least one detector of the first plurality of detectors is positioned to face a first surface of a head of the patient and at least one additional detector of the first plurality of detectors is positioned to face a second, opposite surface of the head of the patient, and wherein the second plurality of detectors is arranged within a second, different two-dimensional detection array disposed on the internal surface of the housing, the method comprising:
    using a standard model for a body shape of at least one part area of the patient;
    detecting first distance data by the first and second plurality of detectors, wherein the first distance data comprises distances between the patient and each detector of the first and second plurality of detectors;
    determining, using the first distance data, a patient model that is deviatable from the standard model for the body shape of the at least one part area of the patient;
    detecting, by the first and second plurality of detectors, further distance data during the magnetic resonance examination of the patient;
    determining the three-dimensional movement of the patient based on the first distance data for the patient model and the further distance data; and
    evaluating medical image data using the three-dimensional movement of the patient, therein reducing artifacts in at least one medical slice image of the medical image data.

10. The method of claim 9, wherein each detector of the first plurality of detectors comprises a position sensitive device (PSD) sensor.

* * * * *